(12) United States Patent
Merschon et al.

(10) Patent No.: US 11,324,419 B2
(45) Date of Patent: May 10, 2022

(54) GRAPHICAL USER INTERFACE FOR MEDICAL IMAGING SYSTEM

(71) Applicant: BIOSENSE WEBSTER (ISRAEL) LTD., Yokneam (IL)

(72) Inventors: Asaf Merschon, Karkur (IL); Moshe Ingel, Haifa (IL); Liav Moshe Adi, Haifa (IL); Eduard Filipov, Karmiel (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 354 days.

(21) Appl. No.: 14/336,366

(22) Filed: Jul. 21, 2014

(65) Prior Publication Data

US 2015/0057529 A1    Feb. 26, 2015

Related U.S. Application Data

(60) Provisional application No. 61/867,664, filed on Aug. 20, 2013.

(51) Int. Cl.
*A61B 5/06* (2006.01)
*A61B 5/00* (2006.01)
(Continued)

(52) U.S. Cl.
CPC .............. *A61B 5/061* (2013.01); *A61B 5/743* (2013.01); *A61B 34/25* (2016.02); *A61B 5/0538* (2013.01);
(Continued)

(58) Field of Classification Search
CPC ....... A61B 34/25; A61B 5/0402; A61B 5/042; A61B 5/0538; A61B 5/061; A61B 5/062; A61B 5/063; A61B 5/7425; A61B 5/743
See application file for complete search history.

(56) References Cited

U.S. PATENT DOCUMENTS 5,433,198 A * 7/1995 Desai .................. A61B 5/0422
600/374
6,049,732 A * 4/2000 Panescu ............... A61B 5/0422
600/427
(Continued)

FOREIGN PATENT DOCUMENTS

EP    1876985 A1    11/2006
JP    2009-106633 A    5/2009
(Continued)

OTHER PUBLICATIONS

U.S. Appl. No. 61/867,664, filed Aug. 20, 2013.
(Continued)

*Primary Examiner* — Katherine L Fernandez
(74) *Attorney, Agent, or Firm* — Dergosits & Noah LLP; Todd A. Noah (57) ABSTRACT

While obtaining electrophysiologic data from a cardiac catheter a series of visual displays are presented. The displays include a respective current image of the heart and the distal portion of the cardiac catheter therein and further include a catheter icon that represents the distal portion of the cardiac catheter, The catheter icon is separated from the image of the heart in the displays. The catheter icon has indicia that represent functional elements of the cardiac catheter.

18 Claims, 6 Drawing Sheets

(51) Int. Cl.
  *A61B 34/00* (2016.01)
  *A61B 5/0538* (2021.01)
  *A61B 5/283* (2021.01)
  *A61B 5/318* (2021.01)
(52) U.S. Cl.
  CPC .............. *A61B 5/062* (2013.01); *A61B 5/063* (2013.01); *A61B 5/283* (2021.01); *A61B 5/318* (2021.01); *A61B 5/7425* (2013.01)

(56) References Cited

U.S. PATENT DOCUMENTS

| | | | |
|---|---|---|---|
| 6,226,542 B1 | 5/2001 | Reisfeld | |
| 6,301,496 B1 | 10/2001 | Reisfeld | |
| 6,814,733 B2 | 11/2004 | Schwartz | |
| 6,892,091 B1 | 5/2005 | Ben Haim | |
| 6,997,924 B2 | 2/2006 | Schwartz | |
| 7,156,816 B2 | 1/2007 | Schwartz | |
| 7,343,195 B2 | 3/2008 | Strommer | |
| 7,536,218 B2 | 5/2009 | Govari | |
| 7,633,502 B2 | 12/2009 | Willis | |
| 7,756,576 B2 | 7/2010 | Levin | |
| 2003/0018251 A1* | 1/2003 | Solomon | A61B 5/04011 600/427 |
| 2004/0193042 A1* | 9/2004 | Scampini | A61B 8/483 600/424 |
| 2006/0116575 A1* | 6/2006 | Willis | A61B 5/0422 600/434 |
| 2009/0326318 A1* | 12/2009 | Tognaccini | A61B 34/37 600/104 |
| 2010/0280366 A1* | 11/2010 | Arne | A61B 5/046 600/425 |
| 2011/0313414 A1 | 12/2011 | Liu | |
| 2012/0029504 A1* | 2/2012 | Afonso | A61B 18/1492 606/34 |
| 2012/0101552 A1 | 4/2012 | Lazarewicz et al. | |
| 2012/0172795 A1 | 7/2012 | Sandhu et al. | |
| 2013/0274582 A1* | 10/2013 | Afonso | A61B 5/0422 600/374 |
| 2014/0235989 A1 | 4/2014 | Wodlinger et al. | |

FOREIGN PATENT DOCUMENTS

| | | |
|---|---|---|
| JP | 2011-520516 | 7/2011 |
| JP | 2014-506171 | 3/2014 |
| JP | 2014-523776 | 9/2014 |
| WO | WO 98/46149 A1 | 10/1998 |
| WO | WO 09/140291 A2 | 11/2009 |
| WO | WO12/040487 A1 | 3/2012 |
| WO | WO 12/092016 A1 | 7/2012 |

OTHER PUBLICATIONS

European Search Report for corresponding Application No. EP14181347 dated Jan. 20, 2015.
Examination Report for corresponding Australia Application No. 2014213565, dated May 14, 2018.
Office Action for corresponding China Application No. 201410410784.5, dated Oct. 23, 2017.
Notification of Reasons for Refusal for Japan Patent Application No. 2014-166404, dated Jul. 3, 2018.
Office Action for China Patent Application No. 201410410784.5, dated Aug. 17, 2018.

* cited by examiner

GRAPHICAL USER INTERFACE FOR MEDICAL IMAGING SYSTEM

CROSS-REFERENCE TO RELATED APPLICATIONS

This Application claims the benefit of U.S. Provisional Application No. 61/867,664, which is herein incorporated by reference.

BACKGROUND OF THE INVENTION

Field of the Invention

This invention relates to medical imaging systems. More particularly, this invention relates to improvements in cardiac catheterization.

Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include locating and surgically disrupting the origin of the signals causing the arrhythmia, as well as disrupting the conducting pathway for such signals. By selectively ablating cardiac tissue by application of energy via a catheter, it is sometimes possible to interrupt or modify the propagation of unwanted electrical signals from one portion of the heart to another. The ablation process destroys the unwanted electrical pathways by formation of non-conducting lesions.

SUMMARY OF THE INVENTION

Electrical activity in the heart is typically measured by advancing a multiple-electrode catheter to measure electrical activity at multiple points in the heart chamber simultaneously. A graphical user interface integrated with modern imaging systems for monitoring cardiac catheterization presents an abundance of dynamically changing information from the multiple electrodes to the operator, and facilitates efficient processing of the information by the operator.

There is provided according to embodiments of the invention a method for guiding a medical procedure, which is carried out by inserting a cardiac catheter into of a heart of a living subject, and thereafter obtaining electrophysiologic data from the cardiac catheter relating to the heart. While obtaining electrophysiologic data, the method is further carried out by presenting a series of visual displays, the displays including a respective current image of the heart and the distal portion of the cardiac catheter therein and further including a catheter icon that represents the distal portion of the cardiac catheter, The catheter icon is separated from the image of the heart in the displays. The catheter icon has indicia that represent functional elements of the cardiac catheter.

According to one aspect of the method, the catheter icon has an orientation that matches a current orientation of the distal portion of the cardiac catheter in the heart.

According to another aspect of the method, presenting a series of visual displays includes enlarging the catheter icon with respect to the image of the heart.

According to a further aspect of the method, presenting a series of visual displays includes applying respective visual cues to the indicia of the catheter icon, wherein the visual cues encode a status of respective functional elements of the cardiac catheter.

According to yet another aspect of the method, the visual cues comprise at least one of a color and a pattern that is associated with one of the functional elements.

According to yet another aspect of the method, the visual cues comprise a numerical descriptor that is associated with one of the functional elements.

According to still another aspect of the method, the visual cues comprise a shape that is associated with one of the functional elements.

According to an additional aspect of the method, the visual cues comprise a de-emphasis of one of the functional elements.

According to still another aspect of the method, the image of the heart is a functional electroanatomic image.

There is further provided according to embodiments of the invention a data processing system, including a processor, a visual display screen, and a memory accessible to the processor storing programs and data objects therein, The programs include a graphical user interface generator configured to present graphical information on the visual display screen, wherein execution of the programs cause the processor to present a series of visual displays, the displays including a respective current image of the heart and a distal portion of the cardiac catheter and further including a catheter icon that represents the distal portion of the cardiac catheter, the catheter icon being separated from the image of the heart, the catheter icon and having indicia that represent functional elements of the cardiac catheter.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a USB memory, hard drive, electronic media or CD-ROM. The code may be distributed on such media, or may be distributed to users from the memory or storage of one computer system over a network of some type to storage devices on other computer systems for use by users of such other systems.

Although the disclosed embodiments relate specifically to intracardiac catheters and ablation procedures, the principles of the present invention may similarly be applied, mutatis mutandis, to probes of other types, for use in substantially any sort of invasive thermal treatment.

Overview

Figure 1:
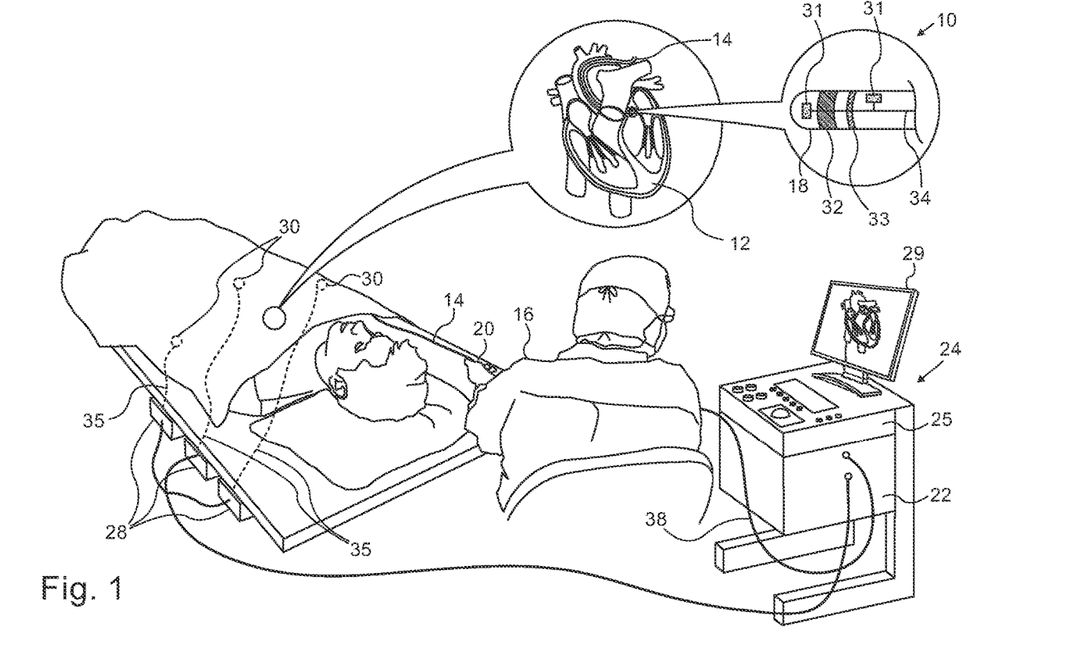
FIG. 1 is a pictorial illustration of a system for performing medical procedures in accordance with an embodiment of the invention.

Turning now to the drawings, reference is initially made to FIG. 1, which is a pictorial illustration of a system 10 for performing diagnostic and therapeutic procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Functional electroanatomic maps, e.g., electrical activation maps may then be prepared, according to the methods disclosed in U.S. Pat. Nos. 6,226, 542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a position processor 22, located in a console 24.

Ablation energy and electrical signals can be conveyed to and from the heart 12 through one or more electrodes 32 located at or near the distal tip 18 via cable 34 to the console 24. Pacing signals and other control signals may be conveyed from the console 24 through the cable 34 and the electrodes 32 to the heart 12. One or more sensing electrodes 33, also connected to the console 24, are disposed near the ablation electrode 32 and have connections to the cable 34.

Wire connections 35 link the console 24 with body surface electrodes 30 and other components of a positioning sub-system. The electrodes 32 and the body surface electrodes 30 may be used to measure tissue impedance at the ablation site as taught in U.S. Pat. No. 7,536,218, issued to Govari et al., which is herein incorporated by reference. A temperature sensor such as thermocouples 31, may be mounted on or near the ablation electrode 32 and optionally or near the sensing electrodes 33. The thermocouples 31 are connected to the electrode circuit as described in further detail below.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to execute a graphical user interface program that is operative to produce the visual displays described below by driving a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14, and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

In order to accurately ablate tissue, for example according to known procedures in which tissue temperature is an important variable, it is desirable to understand and model the behavior of the ablation catheter in actual operation.

Figure 9:
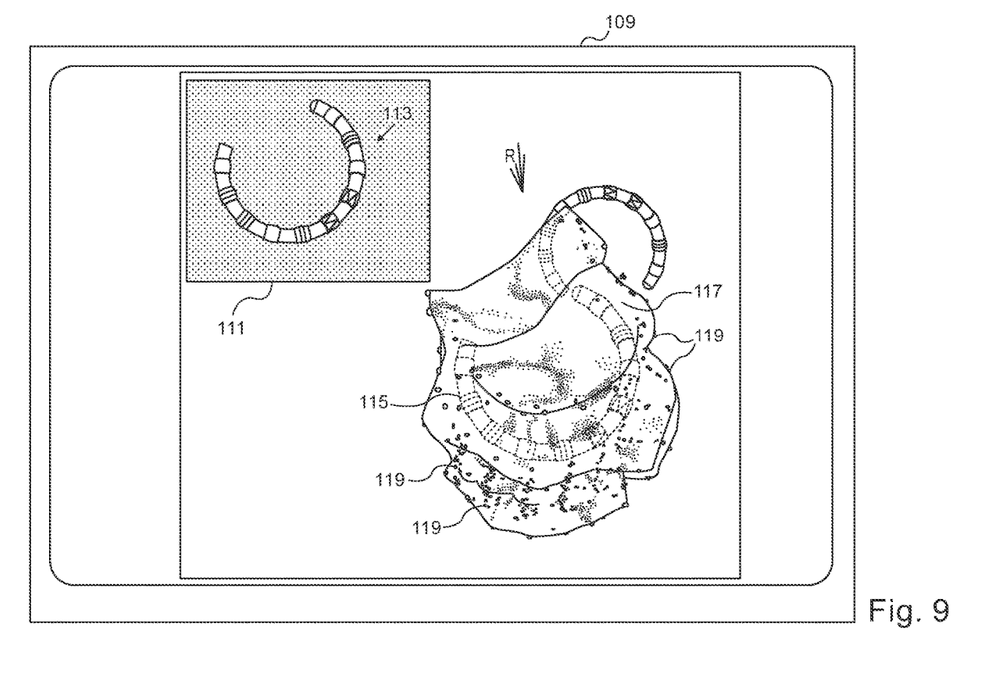
FIG. 9, is an exemplary screen display produced during a cardiac catheterization in accordance with an embodiment of the invention.

With modern imaging systems used for monitoring cardiac catheterization, an increasing abundance of dynamically changing information is presented to the operator, to the extent that efficient processing of the information by the operator is impaired. Modern navigation and ablation catheters typically have multiple sensors, sensing electrodes, and ablation electrodes, which can be active in many combinations. Each of these has its own time-varying status, which is important for the operator to evaluate concurrently with extensive electroanatomic information regarding cardiac function. The graphical image in the example of FIG. 9 illustrates the nature of the difficulties confronting the operator using a known imaging system. An iconic representation of the catheter is embedded within an electroanatomic or functional map of the heart. The catheter has a plurality of elements, e.g., sensors and electrodes. Some of which are numbered and others of which are emphasized with visual cues such as circles and geometric patterns imposed on the elements. The visual cues encode the current status of the particular element and are meaningful to the operator. However, the cues are partially obscured by the functional map, and are sometimes difficult for the operator to appreciate.

User Interface

Figure 2:
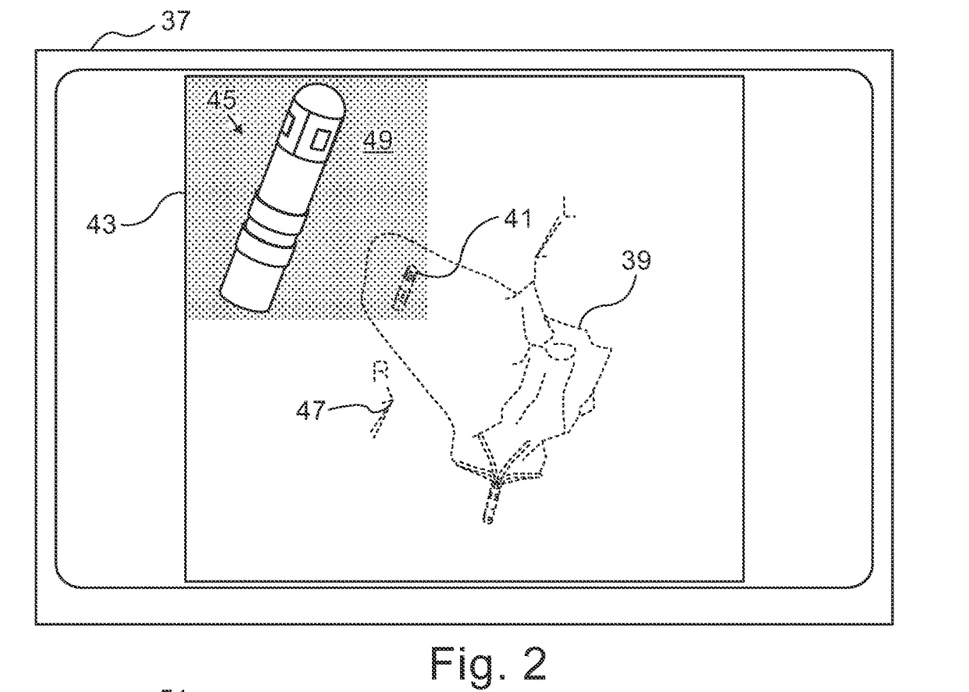
FIG. 2 is a screen display in accordance with an embodiment of the invention.

Reference is now made to FIG. 2, which is a screen display 37, in accordance with an embodiment of the invention. This and the following screen displays may appear on the monitor 29 during a catheterization procedure. Heart 39 is outlined in broken lines. A representation of the distal portion of a catheter 41 is shown within the heart 39 in a particular location and orientation. A separate icon 43 appears in the upper left portion of the screen, and contains a scaled-up catheter image 45 of the distal portion of the catheter 41. In FIG. 2, the catheter image 45 matches the orientation and perspective of the catheter 41. This is not essential, however. A freewheeling mode of operation may be chosen by the operator, in which case the catheter image 45 may be rotated in any axis to an operator-selected orientation independently of the orientation of the catheter 41.

Because the catheter 41 and the icon 43 are separated from the image of the heart 39, the icon 43 is not obscured by the heart. This contrasts to the difficulty of appreciating details of the catheter 41 within the superimposed image of the heart 39 in the central part of the screen display 37. As noted above, this is particularly true of information regarding the status of functional elements of the catheter 41 that may be required to represent the anatomy and electrical events in the heart 39. Such information, while not seen in the figures for clarity of presentation, can in practice be quite extensive and detailed, e.g., pseudocolors, data points, numerical information. The presentation of the heart 39, while desirable and indeed, necessary, nevertheless obscures the catheter 41, whose detailed status information needs to be presented to the operator. The matching orientations of the catheter 41 and the icon 43 may be referenced to a 3-dimensional coordinate system 47

The position of the icon 43 in the upper left corner is exemplary. The actual position and scaling factor are configurable or controllable by the operator, such that the icon 43 is conveniently placed, yet does not interfere with the representation of the heart. Optional visual emphasis, indicated in FIG. 2 by shaded region 49, may be provided for the icon 43 to aid the operator.

Generating the catheter image 45 within the icon 43 may be accomplished by rendering the catheter a first time in the main window (within a 3-dimensional view of the heart 39), then rendering the catheter a second time as the catheter image 45 within the icon 43, preserving its axial rotation and longitudinal orientation. The catheter image 45 is scaled such that the catheter's bounding box (the largest main diagonal of the bounding box of the catheter 41) fits within the icon view.

Figure 3:
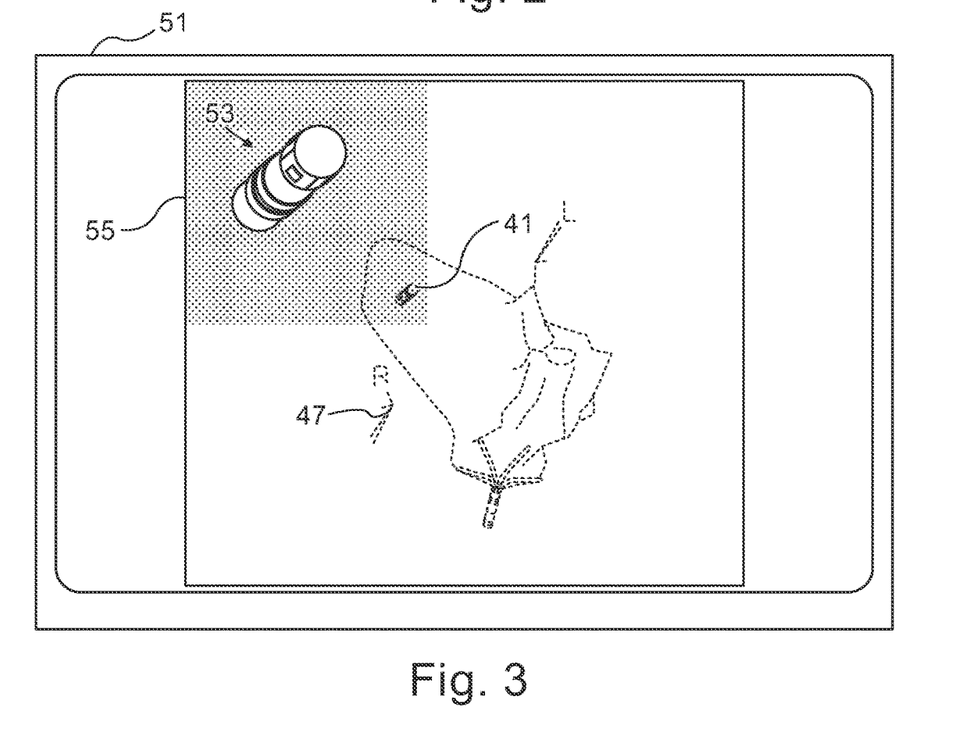
FIG. 3 is a screen display in accordance with an embodiment of the invention.

Reference is now made to FIG. 3, which is a screen display 51 in accordance with an embodiment of the invention. The screen display 51 is similar to the screen display 37 (FIG. 2), except that the catheter 41 has a different orientation with respect to the coordinate system 47. The new orientation is reflected in the orientation of catheter image 53 of the distal portion of the catheter 41 in icon 55.

First Alternate Embodiment

Figure 4:
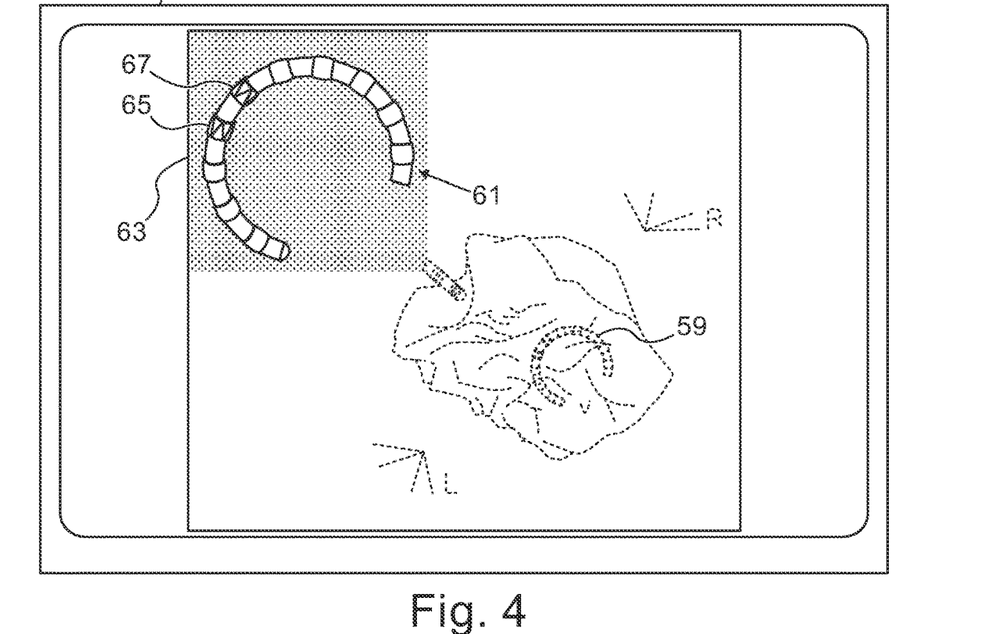
FIG. 4 is a screen display in accordance with an alternate embodiment of the invention.

Reference is now made to FIG. 4, which is a screen display 57 in accordance with an embodiment of the invention. The screen display 51 is similar to the screen display 37 (FIG. 2), except that catheter 59 is a loop or lasso having multiple ring electrodes, as best seen in a catheter image 61 in icon 63. Ring electrodes 65, 67 (shown in hatched pattern) are visually apparent as being actively in use as bipolar sensors.

Figure 5:
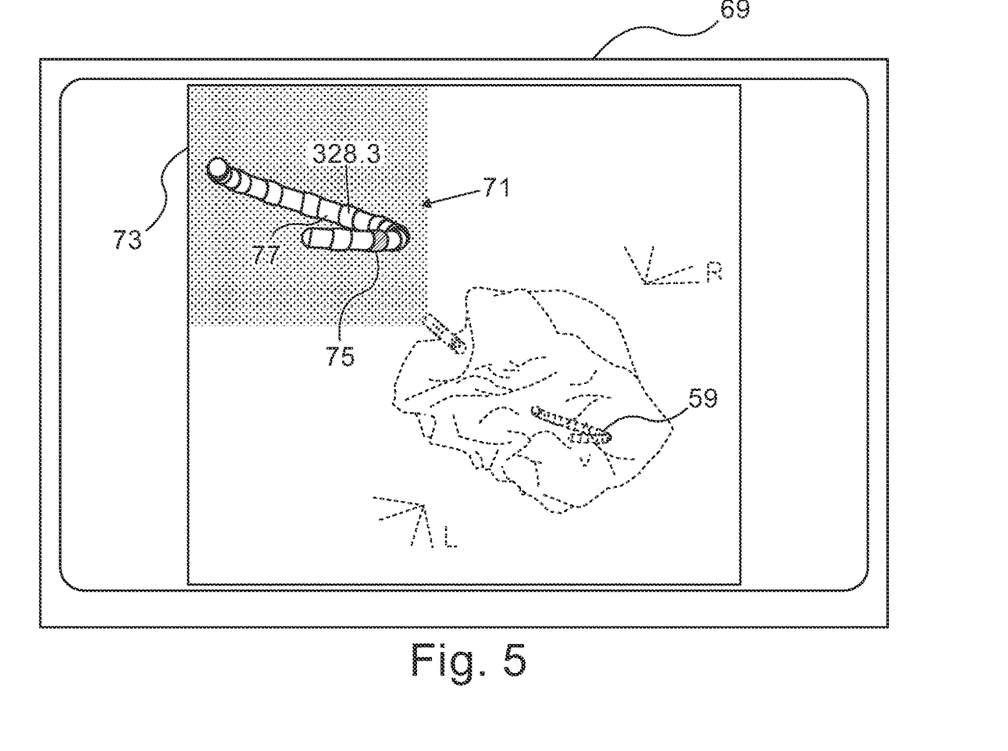
FIG. 5 is a screen display in accordance with an alternate embodiment of the invention.

Reference is now made to FIG. 5, which is a screen display 69 in accordance with an embodiment of the invention. The screen display 69 is similar to the screen display 57 (FIG. 4), except that the catheter 59 has a different orientation, having a partial spiral twist. In the catheter image 71 within icon 73, one ring electrode 75 is currently active, and is readily distinguished from its fellows by a visual effect, indicated here by a hatching pattern. Status information (328.3) is displayed with respect to another ring electrode 77. It will be appreciated that such detail would be less well seen by the operator if it were shown only on the catheter 59.

Second Alternate Embodiment

Figure 6:
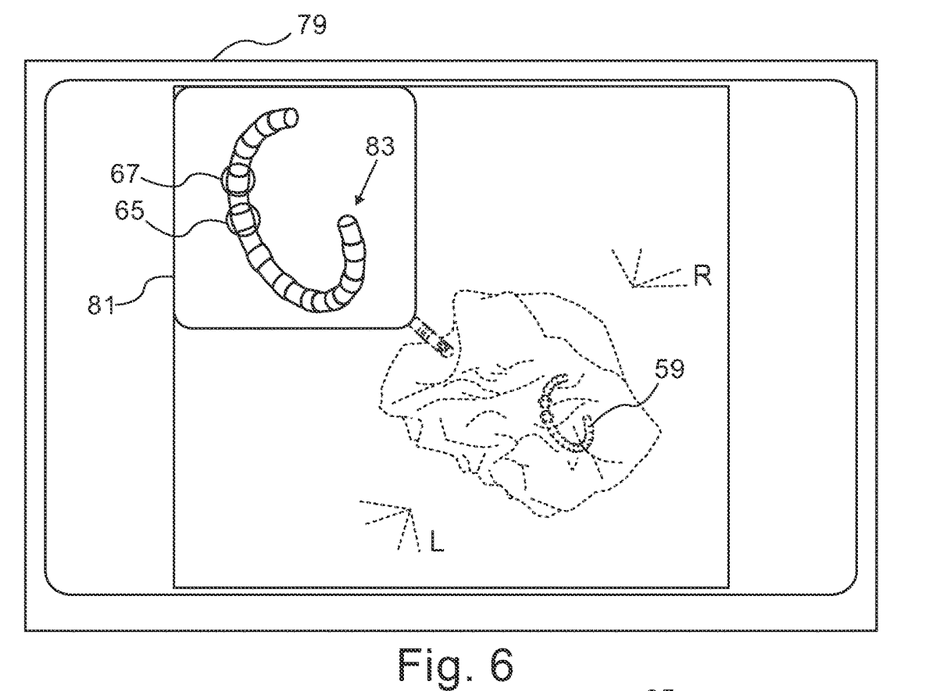
FIG. 6 is a screen display in accordance with an alternate embodiment of the invention.

Reference is now made to FIG. 6, which is a screen display 79 in accordance with an alternate embodiment of the invention. This embodiment is similar to the embodiment shown in FIG. 5, except now in icon 81 the ring electrodes 65, 67 in catheter image 83 are visually emphasized by visual cues (circles). Alternatively, when the cued elements are sensors, such cues could indicate a normal or abnormal functional status; e.g., insufficient or excessive pressure or temperature. As the status of the electrodes and sensors changes dynamically during the procedure, it is important that the operator be alerted to abnormal conditions.

Third Alternate Embodiment

Figure 7:
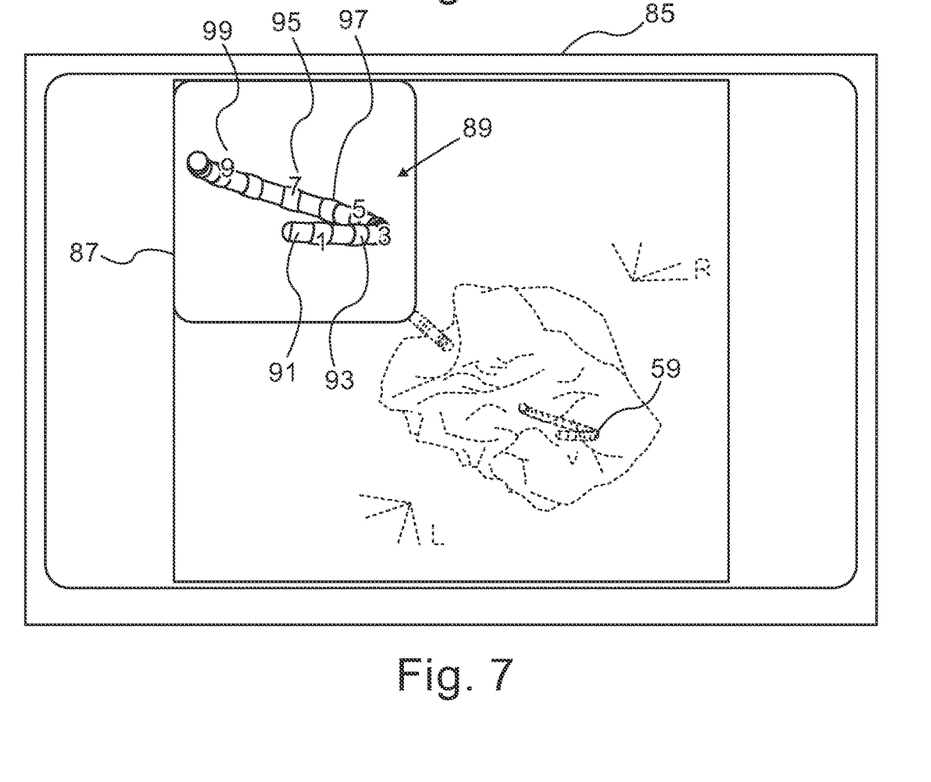
FIG. 7 is a screen display in accordance with an alternate embodiment of the invention.

Reference is now made to FIG. 7, which is a screen display 85 in accordance with an alternate embodiment of the invention. This embodiment is similar to the embodiment shown in FIG. 4. Icon 87 includes catheter image 89 However ring electrodes 91, 93, 95, 97, 99 are now associated with numbers. Numerical indicia of this sort may be correlated with tabular information or the like that is external to the screen display. Additionally or alternatively, such numbers may indicate actual readings of sensors or the current passing through an ablation electrode. Many types of useful sensors may be incorporated in the catheter and their condition represented on the catheter image 89.

Fourth Alternate Embodiment

Figure 8:
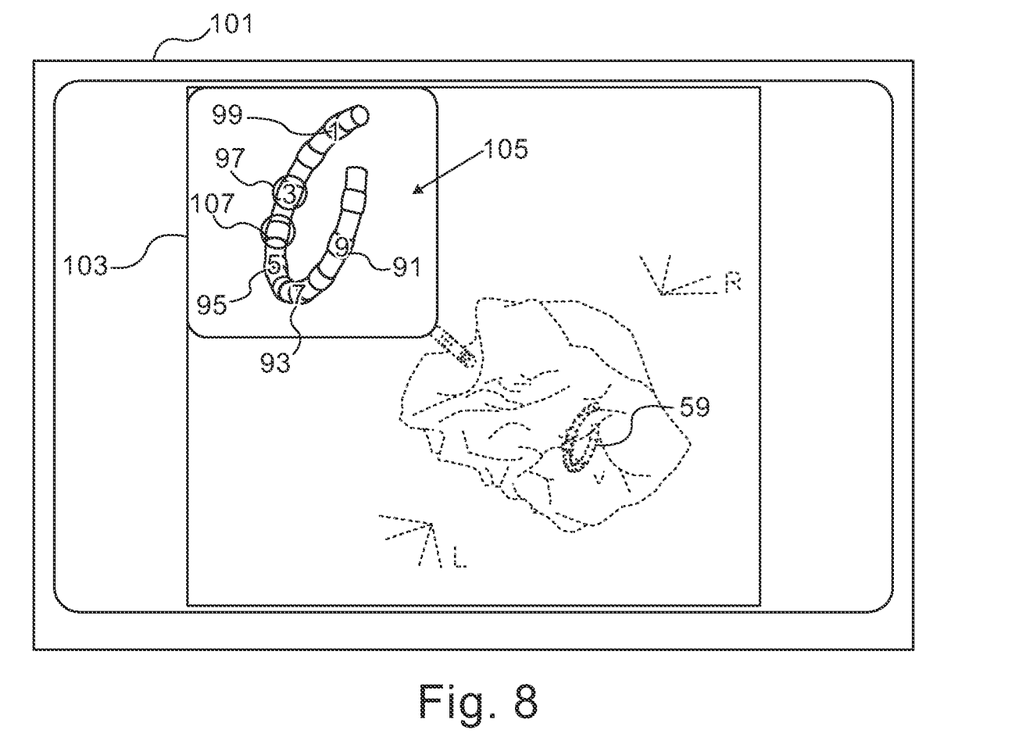
FIG. 8 is a screen display in accordance with an alternate embodiment of the invention.

Reference is now made to FIG. 8, which is a screen display 101 in accordance with an alternate embodiment of the invention. Icon 103 includes catheter image 105. This embodiment is similar to the embodiment shown in FIG. 7. Ring electrodes 91, 93, 95, 97, 99 are associated with numerical indicia as in FIG. 7. Ring electrode 107 is emphasized by a visual cue as in FIG. 6. This embodiment illustrates the versatility that is possible when presenting the icon 103. Many other visual cues will occur to those skilled in the art, e.g., emphasis of catheter elements by highlighting, flashing, and de-emphasis by graying-out.

Example

Reference is now made to FIG. 9, which is an exemplary screen display 109 produced by the above-referenced CARTO 3 system during a cardiac catheterization in accordance with an embodiment of the invention. A functional electroanatomic map of the heart is displayed in pseudocolors, in which local activation times are represented by different hatching and shading patterns in FIG. 9. The screen display 109 includes icon 111 and catheter image 113 in accordance with an embodiment of the invention. Lasso catheter 115 within heart 117 is partially obscured by the electroanatomic map detail and a data point cloud (dots 119) previously obtained during mapping by ring electrodes of the catheter 115. The orientation of the catheter 115 and indications of the status of its ring electrodes can be appreciated by the orientation and the various visual cues in the catheter image 113.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method for guiding a medical procedure, comprising the steps of:
   inserting a cardiac catheter into a heart of a living subject, the cardiac catheter having functional elements disposed on a distal portion thereof;
   obtaining, contemporaneously, electrophysiologic data and image data from the cardiac catheter relating to the heart; and
   presenting in a first window on a single monitor a series of visual displays while contemporaneously obtaining the electrophysiologic data and image data with the cardiac catheter, the series of visual displays in the first window including, in a main window portion of the first window, a 3-dimensional (3-D) image of the heart and a contemporaneous first-time 3-D rendering of only the cardiac catheter therein, the first-time 3-D rendering including the distal portion of the cardiac catheter having a particular perspective and orientation, the 3-D image of the heart concurrently obtained and presented contemporaneously with obtaining the electrophysiologic data, the series of visual displays further including, in an icon portion of the first window, only a second-time 3-D rendering of a scaled-up image of the distal portion of the cardiac catheter as contemporaneously rendered in the main window portion, the second-time 3-D rendering initially matching the orientation and perspective of the cardiac catheter contemporaneously rendered in the main window portion, the distal portion of the cardiac catheter rendered in the icon portion being separated from the 3-D image of the heart in the main window portion when displayed on the single monitor.

2. The method according to claim 1, wherein the distal portion of the catheter in the icon portion has an orientation that matches a current orientation of the distal portion of the cardiac catheter in the heart.

3. The method according to claim 1, wherein presenting the series of visual displays comprises enlarging the distal portion of the catheter in the icon portion with respect to the 3-D image of the heart.

4. The method according to claim 1, wherein presenting the series of visual displays comprises applying respective visual cues to indicia of functional elements of the catheter in the icon portion, wherein the visual cues encode a status of respective functional elements of the cardiac catheter.

5. The method according to claim 4, wherein the visual cues comprise at least one of a color and a pattern that is associated with one of the functional elements.

6. The method according to claim 4, wherein the visual cues comprise a numerical descriptor that is associated with one of the functional elements.

7. The method according to claim 4, wherein the visual cues comprise a shape that is associated with one of the functional elements.

8. The method according to claim 4, wherein the visual cues comprise a de-emphasis of one of the functional elements.

9. The method according to claim 1, wherein the 3-D image of the heart comprises a functional electroanatomic image.

10. A data processing system comprising:
    a processor;
    a single monitor having a visual display screen; and
    a memory accessible to the processor storing programs and data objects therein, the programs including a graphical user interface generator configured to present graphical information on the visual display screen, wherein execution of the programs cause the processor to perform the steps of:
    presenting in a first window on the single monitor a series of visual displays while contemporaneously obtaining electrophysiologic data and image data from a heart with a cardiac catheter, the series of visual displays including, in a main window portion of the first window a respective 3-dimensional (3-D) image of the heart and a contemporaneous 3-D first-time rendering of only the cardiac catheter therein, the first-time 3-D rendering including the distal portion of the cardiac catheter having a particular perspective and orientation, the 3-D image of the heart concurrently obtained and presented contemporaneously with obtaining the electrophysiologic data, the series of visual displays further including, in an icon portion of the first window, only a second-time 3-D rendering of a scaled-up image of the distal portion of the cardiac catheter as contemporaneously rendered in the main window portion, the second-time 3-D rendering initially matching the orientation and perspective of the cardiac catheter contemporaneously rendered in the main window portion, the distal portion of the catheter rendered in the icon portion being separated from the 3-D image of the heart in the main window portion when displayed on the single monitor, the distal tip of the catheter in the icon portion having indicia that represent functional elements of the cardiac catheter.

11. The system according to claim 10, wherein the distal portion of the catheter in the icon portion has an orientation that matches a current orientation of the distal portion of the cardiac catheter in the heart.

12. The system according to claim 10, wherein presenting the series of visual displays comprises enlarging the distal portion of the catheter in the icon portion with respect to the 3-D image of the heart.

13. The system according to claim 10, wherein presenting the series of visual displays comprises applying respective visual cues to the indicia of the functional elements of the catheter in the icon portion, wherein the visual cues encode a status of respective functional elements of the cardiac catheter.

14. The system according to claim 13, wherein the visual cues comprise at least one of a color and a pattern that is associated with one of the functional elements.

15. The system according to claim 13, wherein the visual cues comprise a numerical descriptor that is associated with one of the functional elements.

16. The system according to claim 13, wherein the visual cues comprise a shape that is associated with one of the functional elements.

17. The system according to claim 13, wherein the visual cues comprise a de-emphasis of one of the functional elements.

18. The system according to claim 10, wherein the 3-D image of the heart comprises a functional electroanatomic image.

* * * * *